US011298207B2

(12) United States Patent
Gliner et al.

(10) Patent No.: US 11,298,207 B2
(45) Date of Patent: Apr. 12, 2022

(54) MEDICAL INSTRUMENT IDENTIFICATION

(71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 350 days.

(21) Appl. No.: 16/375,485

(22) Filed: Apr. 4, 2019

(65) Prior Publication Data

US 2020/0315741 A1 Oct. 8, 2020

(51) Int. Cl.
*A61B 90/98* (2016.01)
*A61B 34/20* (2016.01)
(Continued)

(52) U.S. Cl.
CPC .............. *A61B 90/98* (2016.02); *A61B 17/24* (2013.01); *A61B 17/320016* (2013.01);
(Continued)

(58) Field of Classification Search
CPC ......... A61B 90/36; A61B 90/37; A61B 90/39; A61B 90/90; A61B 90/98; A61B 2090/0805; A61B 2090/365; A61B 2090/3983; A61B 34/20; A61B 2034/2046; A61B 2034/2051; A61B 2034/2055; A61B 2034/2065; A61B 2034/2072; A61B 2017/0046; A61B 2017/00464; A61B 2017/00473; A61B 17/320016; G01B 7/00; G01B 7/004; G01B 7/02; G01B 7/023;
(Continued)

(56) References Cited

U.S. PATENT DOCUMENTS 8,000,772 B2 8/2011 Govari et al.
8,600,478 B2 12/2013 Verard et al.
(Continued)

OTHER PUBLICATIONS

European Search Report dated Jul. 22, 2020 from corresponding European Patent Application No. 20167892.7.

*Primary Examiner* — Robert A Lynch
(74) *Attorney, Agent, or Firm* — Frost Brown Todd LLC

(57) ABSTRACT

In one embodiment, a medical instrument tracking system includes a medical instrument including a handle and different interchangeable heads for insertion into the handle having a handle position-tracking transducer disposed thereon, different respective ones of the interchangeable heads having differently positioned respective head position-tracking transducers disposed thereon so as when the different respective ones of the heads are inserted into the handle, the different respective head position-tracking transducers define different respective positions relative to the handle position-tracking transducer, and processing circuitry to receive signals generated by the handle position-tracking transducer and the respective head position-tracking transducer of a respective one of the heads inserted into the handle, compute a relative position between the handle position-tracking transducer and the head position-tracking transducer of the inserted interchangeable head, and identify which interchangeable head is inserted into the handle responsively to the computed relative position.

23 Claims, 7 Drawing Sheets

(51) Int. Cl.
*A61B 90/00* (2016.01)
*A61B 17/24* (2006.01)
*A61B 17/32* (2006.01)
*A61B 17/00* (2006.01)

(52) U.S. Cl.
CPC .............. *A61B 34/20* (2016.02); *A61B 90/37* (2016.02); *A61B 2017/00464* (2013.01); *A61B 2034/2051* (2016.02); *A61B 2034/2072* (2016.02)

(58) Field of Classification Search
CPC ........ G01B 21/00; G01B 21/02; G01B 21/04; G01B 21/047
See application file for complete search history.

(56) References Cited

U.S. PATENT DOCUMENTS

| | | | | |
|---|---|---|---|---|
| 9,393,079 | B2 | 7/2016 | Weese et al. | |
| 9,622,824 | B2 | 4/2017 | Goldbach | |
| 2007/0080682 | A1 | 4/2007 | Govari et al. | |
| 2008/0021311 | A1* | 1/2008 | Goldbach | A61B 34/20 600/426 |
| 2008/0200927 | A1 | 8/2008 | Hartmann et al. | |
| 2010/0210939 | A1 | 8/2010 | Hartmann et al. | |
| 2013/0267833 | A1 | 10/2013 | Schroeder | |

* cited by examiner

MEDICAL INSTRUMENT IDENTIFICATION

FIELD OF THE INVENTION

The present invention relates to medical instruments, and in particular, but not exclusively to medical instrument identification.

BACKGROUND

Automatic identification of a medical instrument is known in the art. For example, U.S. Pat. No. 9,622,824 to Goldbach describes a method for using a medical navigation system to identify an instrument to be navigated, wherein the instrument includes a reference array having a plurality of markers that form a rigid body, and a location of the markers with respect to each other is not previously known in the navigation system as a characteristic arrangement for a particular instrument. The method includes measuring a distance of each marker relative to the other markers; identifying a spatial arrangement of the markers having the measured distance as an assignable marker array; assigning the assignable marker array to the instrument; and identifying the instrument based on the assigned marker array.

U.S. Pat. No. 9,393,079 to Weese, et al., describes a method and an image processing system for the evaluation of projection images generated by an X-ray imaging system, wherein the images may show different instruments of a given set of interventional instruments like catheters or guide wires. The instruments are equipped with markers such that their configuration is characteristic of the corresponding instrument. Preferably three markers are arranged on a straight line, the ratio of the distances between them being characteristic for the corresponding instrument. The image processing system may then identify the instruments present in a given projection and provide functionalities for a user that correspond to said instruments. Moreover, the system may be used to locate an instrument of interest in a projection image if the marker configuration of that instrument is known a priori.

US Patent Publication 2008/0200927, issued as U.S. Pat. No. 8,233,963 on Jul. 31, 2012, of Hartmann, et al., describes a method and apparatus for identifying a member used in a navigation system. The navigation system can determine the identification of an instrument via an input. The input can be substantially automatic when an instrument is introduced into the navigation system field or assembly.

U.S. Pat. No. 8,600,478 to Verard, et al., describes a system and apparatus to determine the identification and selected information relating to surgical instruments near a reader. The information can be stored on a member operable to transmit the information to a reader at a selected time. The information can be used in a navigation system to assist in navigation of the instrument relative to a patient.

US Patent Publication 2007/0080682, issued as U.S. Pat. No. 7,301,332 on Nov. 27, 2007, of Govari, et al., describes a sensor assembly includes a first magneto-resistive field sensor in a first surface-mountable package, which measures first and second components of a magnetic field projected onto respective different first and second axes with respect to a spatial orientation of the sensor and to produce first position signals indicative of the measured first and second components. A second magneto-resistive field sensor in a second surface-mountable package measures at least a third component of the magnetic field projected onto at least a third axis with respect to the spatial orientation of the sensor, and to produce second position signals indicative of the measured third component. A substrate assembly orients the first field sensor in a first spatial orientation and to orient the second field sensor in a second spatial orientation so that the third axis is oriented out of a plane containing the first and second axes.

SUMMARY

There is provided in accordance with an embodiment of the present disclosure, a medical instrument tracking system, including a medical instrument including a handle and different rigid interchangeable heads for individual insertion into the handle, the handle having a handle position-tracking transducer disposed thereon, different respective ones of the interchangeable heads having differently positioned respective head position-tracking transducers disposed thereon so as when the different respective ones of the interchangeable heads are inserted into the handle, the different respective head position-tracking transducers define different respective positions relative to the handle position-tracking transducer, and processing circuitry configured to receive signals generated by the handle position-tracking transducer and the respective head position-tracking transducer of a respective one of the interchangeable heads inserted into the handle, compute a relative position between the handle position-tracking transducer and the head position-tracking transducer of the inserted interchangeable head responsively to the received signals, and identify which one of the interchangeable heads is inserted into the handle responsively to the computed relative position.

Further in accordance with an embodiment of the present disclosure the interchangeable heads are different from each other with respect to at least any one or more of the following a head shape, or a head size.

Still further in accordance with an embodiment of the present disclosure the processing circuitry is configured to detect whether the inserted interchangeable head is inserted correctly into the handle responsively to the computed relative position.

Additionally, in accordance with an embodiment of the present disclosure the computed relative position includes a computed distance between the handle position-tracking transducer and the head position-tracking transducer of the inserted interchangeable head, the processing circuitry being configured to identify which one of the interchangeable heads is inserted into the handle responsively to at least the computed distance.

Moreover in accordance with an embodiment of the present disclosure the handle includes multiple rotational positions in which to insert the different rigid interchangeable heads, the computed relative position includes a computed orientation of the head position-tracking transducer of the inserted interchangeable head relative to the handle position-tracking transducer, the processing circuitry being configured to identify which one of the interchangeable heads is inserted into the handle responsively to the computed distance and the computed orientation.

Further in accordance with an embodiment of the present disclosure the handle includes multiple rotational positions to which to rotate the different rigid interchangeable heads, the computed relative position including a computed orientation of the head position-tracking transducer of the inserted interchangeable head relative to the handle position-tracking transducer, the processing circuitry being configured to identify which one of the interchangeable heads is inserted into the handle responsively to the computed distance and the computed orientation.

Still further in accordance with an embodiment of the present disclosure each of the interchangeable heads includes at least one cutting element.

Additionally in accordance with an embodiment of the present disclosure the medical instrument is configured for inserting into a body part of a living subject, the system further including a location pad having at least one magnetic field radiator configured to transmit alternating magnetic fields into a region where the body-part is located, the head position-tracking transducer of each of the interchangeable heads including at least one coil configured to detect at least part of the transmitted alternating magnetic fields.

Moreover, in accordance with an embodiment of the present disclosure the head position-tracking transducer of each of the interchangeable heads is a dual axis transducer printed on a circuit board.

Further in accordance with an embodiment of the present disclosure the medical instrument is configured for inserting into a body part of a living subject, the system further including a display, the processing circuitry being configured to track a location of the inserted interchangeable head responsively to at least some of the received signals, and render to the display an image including a representation of at least part of the body part and a representation of at least part of the inserted interchangeable head of the medical instrument in the body part responsively to the tracked location and a shape and size of the identified inserted interchangeable head.

There is also provided in accordance with another embodiment of the present disclosure, a medical instrument tracking system, including a medical instrument including a handle and different rigid interchangeable heads for individual insertion into the handle, the handle having a handle position-tracking transducer disposed thereon, different respective ones of the interchangeable heads having differently positioned respective head position-tracking transducers disposed thereon so as when the different respective ones of the interchangeable heads are inserted into the handle, the different respective head position-tracking transducers define different respective positions relative to the handle position-tracking transducer, and processing circuitry configured to receive signals generated by the handle position-tracking transducer and the respective head position-tracking transducer of a respective one of the interchangeable heads inserted into the handle, compute a relative position between the handle position-tracking transducer and the head position-tracking transducer of the inserted interchangeable head responsively to the received signals, receive a user identification of the inserted interchangeable head via a user input device, and associate the user identification of the inserted interchangeable head with the computed relative position so as to allow future identification of the inserted interchangeable head being reinserted into the handle responsively to a new computed relative position being within a given tolerance of the computed relative position.

Still further in accordance with an embodiment of the present disclosure the computed relative position includes a computed distance between the handle position-tracking transducer and the head position-tracking transducer of the inserted interchangeable head, the processing circuitry being configured to associate the user identification of the inserted interchangeable head with the computed distance so as to allow future identification of the inserted interchangeable head being reinserted into the handle responsively to at least a new computed distance being within a given tolerance of the computed distance.

Additionally in accordance with an embodiment of the present disclosure the handle includes multiple rotational positions in which to insert the different rigid interchangeable heads, the computed relative position includes a computed orientation of the head position-tracking transducer of the inserted interchangeable head relative to the handle position-tracking transducer, the processing circuitry being configured to associate the user identification of the inserted interchangeable head with the computed distance and the computed orientation so as to allow future identification of the inserted interchangeable head being reinserted into the handle responsively to a new computed distance and a new computed orientation being within at least one given tolerance of the computed distance and the computed orientation, respectively.

Moreover in accordance with an embodiment of the present disclosure the handle includes multiple rotational positions to which to rotate the different rigid interchangeable heads, the computed relative position including a computed orientation of the head position-tracking transducer of the inserted interchangeable head relative to the handle position-tracking transducer, the processing circuitry being configured to associate the user identification of the inserted interchangeable head with the computed distance and the computed orientation so as to allow future identification of the inserted interchangeable head being reinserted into the handle responsively to a new computed distance and a new computed orientation being within at least one given tolerance of the computed distance and the computed orientation, respectively.

There is also provided in accordance with still another embodiment of the present disclosure, a method for medical treatment using a medical instrument including a handle and different rigid interchangeable heads for individual insertion into the handle, the handle having a handle position-tracking transducer disposed thereon, different respective ones of the interchangeable heads having differently positioned respective head position-tracking transducers disposed thereon so as when the different respective ones of the interchangeable heads are inserted into the handle, the different respective head position-tracking transducers define different respective positions relative to the handle position-tracking transducer, the method including receiving signals generated by the handle position-tracking transducer and the respective head position-tracking transducer of a respective one of the interchangeable heads inserted into the handle, computing a relative position between the handle position-tracking transducer and the head position-tracking transducer of the inserted interchangeable head responsively to the received signals, and identifying which one of the interchangeable heads is inserted into the handle responsively to the computed relative position.

Further in accordance with an embodiment of the present disclosure the interchangeable heads are different from each other with respect to at least any one or more of the following a head shape, or a head size.

Still further in accordance with an embodiment of the present disclosure, the method includes detecting whether the inserted interchangeable head is inserted correctly into the handle responsively to the computed relative position.

Additionally, in accordance with an embodiment of the present disclosure the computed relative position includes a computed distance between the handle position-tracking transducer and the head position-tracking transducer of the inserted interchangeable head, wherein the identifying includes identifying which one of the interchangeable heads is inserted into the handle responsively to at least the computed distance.

Moreover in accordance with an embodiment of the present disclosure the handle includes multiple rotational positions in which to insert the different rigid interchangeable heads, the computed relative position includes a computed orientation of the head position-tracking transducer of the inserted interchangeable head relative to the handle position-tracking transducer, the identifying including identifying which one of the interchangeable heads is inserted into the handle responsively to the computed distance and the computed orientation.

Further in accordance with an embodiment of the present disclosure the handle includes multiple rotational positions to which to rotate the different rigid interchangeable heads, the computed relative position including a computed orientation of the head position-tracking transducer of the inserted interchangeable head relative to the handle position-tracking transducer, the identifying including identifying which one of the interchangeable heads is inserted into the handle responsively to the computed distance and the computed orientation.

Still further in accordance with an embodiment of the present disclosure each of the interchangeable heads includes at least one cutting element.

Additionally in accordance with an embodiment of the present disclosure the medical instrument is configured for inserting into a body part of a living subject, the method further including transmitting alternating magnetic fields into a region where the body-part is located, the head position-tracking transducer of each of the interchangeable heads includes at least one coil, and detecting at least part of the transmitted alternating magnetic fields by the at least one coil.

Moreover, in accordance with an embodiment of the present disclosure the head position-tracking transducer of each of the interchangeable heads is a dual axis transducer printed on a circuit board.

Further in accordance with an embodiment of the present disclosure the medical instrument is configured for inserting into a body part of a living subject, the method further including tracking a location of the inserted interchangeable head responsively to at least some of the received signals, and rendering to a display an image including a representation of at least part of the body part and a representation of at least part of the inserted interchangeable head of the medical instrument in the body part responsively to the tracked location and a shape and size of the identified inserted interchangeable head.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
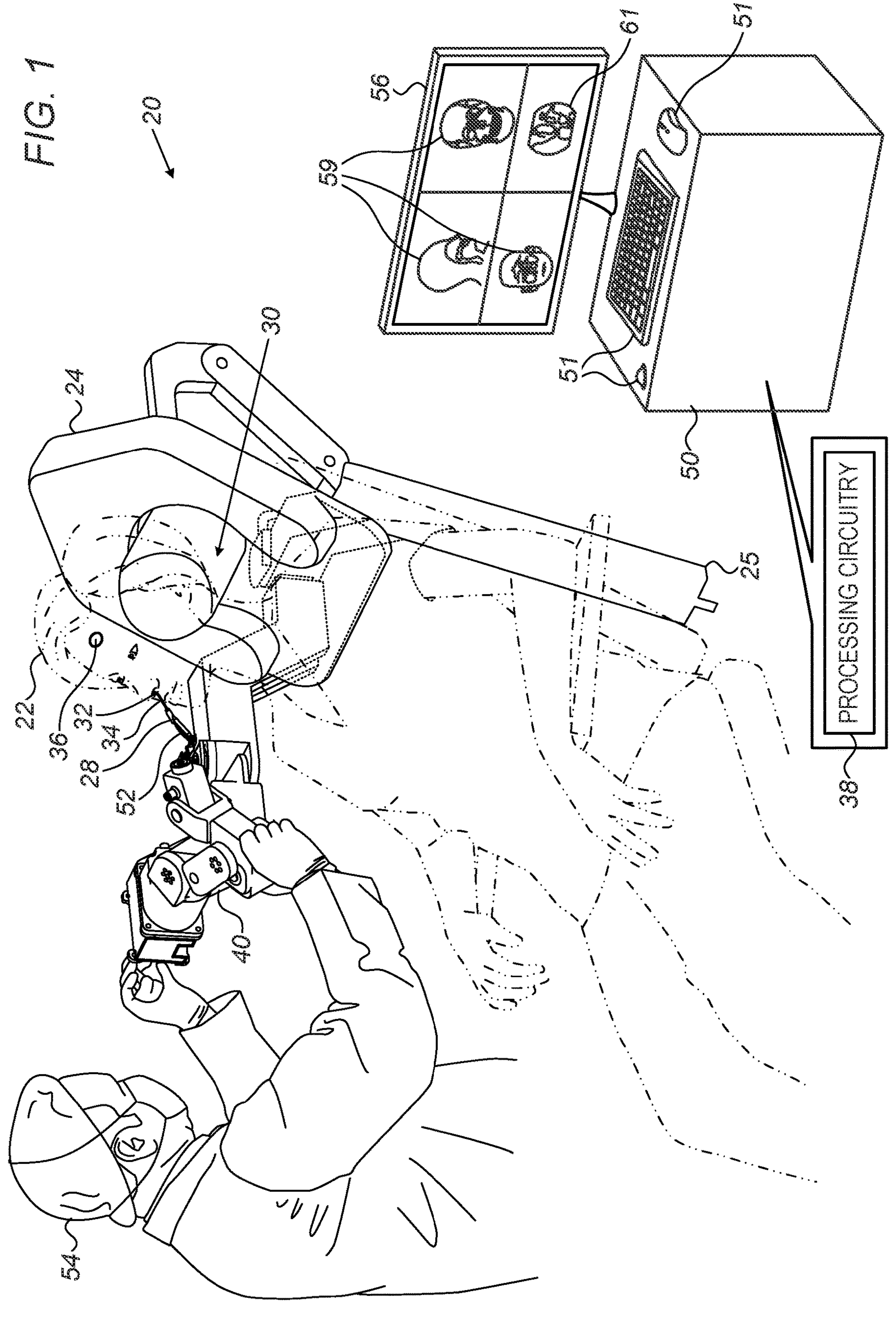
FIG. 1 is a schematic illustration of a medical procedure system, according to an embodiment of the present invention.

Some medical instruments may include a handle with multiple interchangeable rigid heads. The different interchangeable rigid heads may be sized and/or shaped differently to perform different functions and/or access different body-parts. In one such example, the rigid heads may include at their distal end, at least one cutting element such as a rotating blade and/or rotating bur to remove tissue inside a body-part of a living subject. Some of the rigid heads may be generally straight whereas others may include a curved portion.

Some medical instruments may allow the heads to be inserted into the handle in one of many rotational positions. Additionally, or alternatively, some medical instruments may allow the inserted head to be rotated to multiple rotation positions. In such situations, accurately navigating the head of the medical instrument, including roll information, in the body-part by a physician may be challenging. Using a position tracking sensor on the distal tip of the handle of the medical instrument may not provide useful information about the rotational position of the head. Additionally, there may be a substantial distance from the handle to the distal tip of the head and an angular position error compounds the distance error. Additionally, when the head is a metal head, metal interference from the head may further distort readings. Disposing a large and complex sensor as well as a controller (such as an EEPROM) on the head may also be challenging because of lack of room for the controller components and wires.

Additionally, even if the rotational position of the head is not a factor, navigation may require knowledge of which one of the heads is currently inserted into the medical instrument. The physician could manually register which head is being used with the navigation system. However, during a medical procedure the heads may be changed multiple times and manually registering which head is being used with the navigation system takes time and is error prone.

Embodiments of the present invention include a medical instrument having a handle and different rigid interchangeable heads for individual insertion into the handle. The interchangeable heads may be different from each other with respect to a shape and/or a head size and/or a function, by way of example only. In some embodiments, at least some of the heads may include at least one cutting element, by way of example only.

The handle has a handle position-tracking transducer disposed thereon. Each of the interchangeable heads has a head position-tracking transducer disposed thereon. The head position-tracking transducers are strategically placed on the interchangeable heads so that when each interchangeable head is individually inserted into the handle, the relative position between the handle position-tracking transducer and the head position-tracking transducer of the inserted interchangeable head uniquely identifies the inserted interchangeable head irrespective of the rotational position in which the interchangeable head has been inserted into the handle and irrespective of the rotational position to which the inserted interchangeable head has been rotated.

Therefore, different respective ones of the interchangeable heads have differently positioned respective head position-tracking transducers disposed thereon so as when the different respective ones of the interchangeable heads are inserted into the handle, the different respective head position-tracking transducers define different respective positions relative to the handle position-tracking transducer. In other words, one head when inserted into the handle is associated with a certain relative position (or positions) between its head position-tracking transducer and the handle position-tracking transducer, whereas another head when inserted into the handle is associated with a different relative position (or positions) between its head position-tracking transducer and the handle position-tracking transducer.

The different relative positions of the different heads may be computed in a calibration stage. The computed relative position(s) may then be linked to the associated heads in a lookup table or the like, for future lookup. In such manner, the different relative positions may then be used to identify which of the heads is inserted into the handle, as described below in more detail.

Each head position-tracking transducer may be a dual axis transducer (for example, comprising two orthogonal wound coils) which may track position and orientation, including roll, of the respective head. The dual axis transducer may be printed on a printed circuit board (PCB) for attaching to the head. In some embodiments where the head is fixed with relation to the handle, a single axis transducer may be used. In some embodiments, the handle position-tracking transducer may be a dual or triple axis transducer, by way of example only.

There are several advantages of using a PCB transducer. First, a PCB transducer does not suffer from metal interference. Second, the PCB may be placed very accurately orientation-wise on the head. Third, the PCB transducer is not a wound coil, but is a standard printed coil, so that each PCB has substantially the same magnetic sensitivity. Therefore, based on the above advantages the PCB transducer does not generally need calibration and therefore does not need a controller (e.g., an EEPROM) which is generally too bulky for disposing on the head.

Processing circuitry receives signals generated by the handle position-tracking transducer and the head position-tracking transducer of the interchangeable head inserted into the handle. The processing circuitry computes a relative position (which may include a distance and/or an orientation) between the handle position-tracking transducer and the head position-tracking transducer of the inserted interchangeable head responsively to the received signals. The processing circuitry then identifies which one of the interchangeable heads is inserted into the handle responsively to the computed relative position and the data computed during the calibration stage. The computed relative position may also be used to detect whether the inserted interchangeable head is inserted correctly into the handle based on whether the computed relative position sufficiently correlates with one of the computed relative positions from the calibration data.

The location of the inserted interchangeable head may be tracked responsively to at least some of the received signals from the handle position-tracking transducer and/or the head position-tracking transducer of the inserted head. An image including a representation of at least part of a body part and a representation of at least part of the inserted interchangeable head of the medical instrument in the body part may be rendered to a display responsively to the tracked location and a shape and size of the identified inserted interchangeable head.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
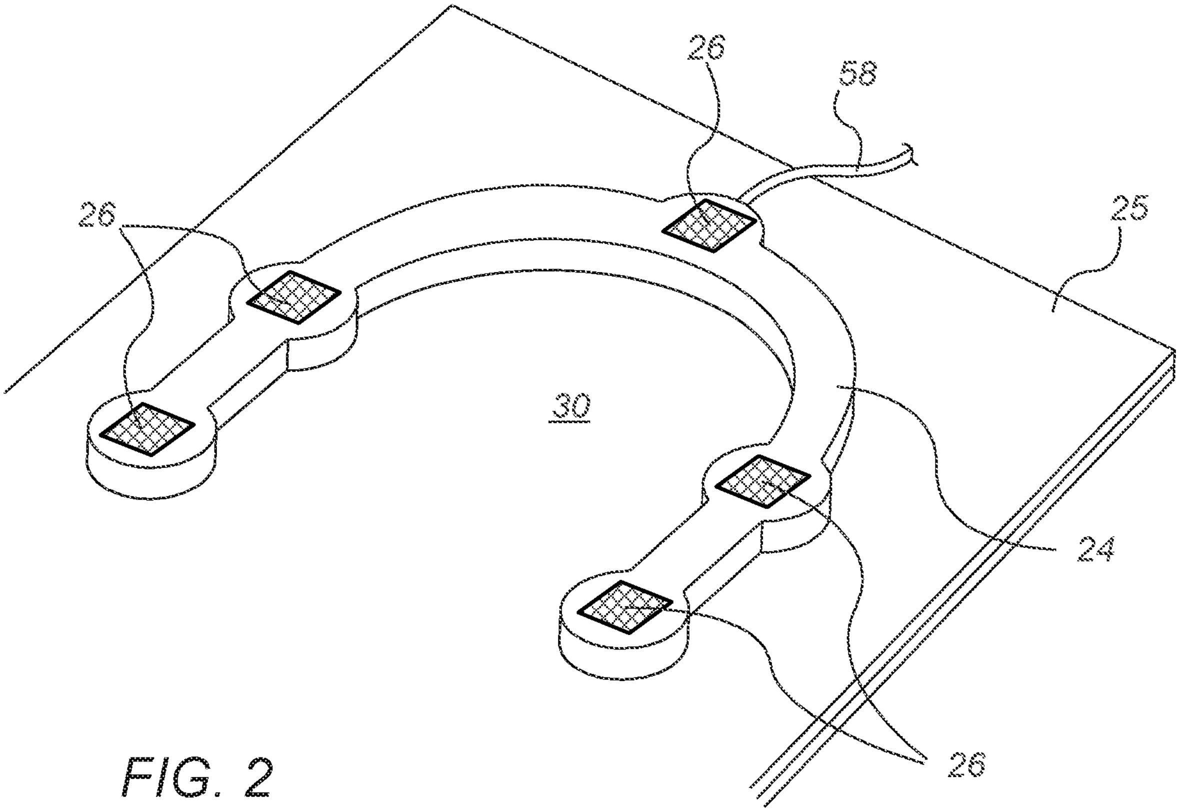
FIG. 2 is a schematic illustration of a magnetic field radiation assembly used in the medical procedure system, according to an embodiment of the present invention.

Turning now to the drawings, reference is now made to FIG. 1, which is a schematic illustration of a medical procedure system 20, and to FIG. 2, which is a schematic illustration of a magnetic field radiation assembly location pad 24 used in the system 20, according to an embodiment of the present invention. The medical procedure system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30 where the body part is located, in proximity to the magnetic field radiation assembly 24 and which includes the head of patient 22.

The alternating magnetic fields induce signals in a position-tracking transducer 32 and a position-tracking transducer 36. The position-tracking transducer 32 is shown disposed on a medical instrument 28 in order to track a position of the medical instrument 28. The position-tracking transducer 36 is shown disposed on the patient 22 (e.g., on the forehead of the patient 22 or any other suitable body part) in order to track a position of the patient 22 (e.g., to track a position of the head of the patient 22) to compensate for movement of the patient with respect to the magnetic field radiation assembly 24. By way of example only, the medical instrument 28 may include any one or more of the following, a probe for inserting into the body-part, an endoscope, and/or a surgical tool such as an ENT tool, suction tool, microdebrider, or a shaver.

The position of the distal end of the medical instrument 28 and the position of the patient 22, may be tracked using a tracking subsystem, which tracks position and orientation coordinates of the position-tracking transducer 32 fitted at the distal end and the position-tracking transducer 36, respectively. The position-tracking transducers 32, 36 are configured to output signals that are indicative of locations of the transducer 32, 36, respectively. The signals are processed by the tracking subsystem running on processing circuitry 38 to track the locations of the distal end of the medical instrument 28 and the position of the patient 22 over time. In embodiments, where the tracking subsystem is a magnetic tracking subsystem, the position-tracking transducer 32 and/or the position-tracking transducer 36 includes at least one coil, described in more detail with reference to FIG. 5. In other embodiments, the tracking subsystem may be an electrically-based tracking subsystem using multiple head surface electrodes (e.g., multiple instances of the position-tracking transducer 36) to track the position of the medical instrument 28 based on a signal emitted by at least one electrode (comprised in the position-tracking transducer 32) of the medical instrument 28. The tracking subsystem may be implemented using any suitable location tracking subsystem, for example, but not limited to, an ultrasound-based tracking system where the position-tracking transducer 32 includes at least one ultrasound transducer. Using tracking subsystem, a physician 54 advances the distal end of the medical instrument 28 in a body-part, described in more detail below.

In some embodiments, the medical instrument 28 is attached to, and held by, a robotic arm 40, which is configured to manipulate the medical instrument 28. The robotic arm 40 includes a plurality of robotic joints configured to control movement of the robotic arm 40 and manipulate the medical instrument 28. In other embodiments, the medical instrument 28 is held and manipulated by the physician 54.

As is described in more detail below, position-tracking transducer 32 is affixed to the medical instrument 28, and determination of the location and orientation of the position-tracking transducer 32 enables tracking the location and orientation of a distal end 34 (or other location) of the medical instrument 28, that may be reversibly inserted into a body-part of the patient 22 (the living subject).

Similarly, determination of the location and orientation of the position-tracking transducer 36 enables the location and orientation of a part (e.g., the head) of the patient 22 to be tracked. The position-tracking transducer 36 is shown in FIG. 1 as being disposed on the forehead of the patient 22. The position-tracking transducer 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, issued as U.S. Pat. No. 10,772,489 on Sep. 15, 2020, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position-tracking transducer 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the processing circuitry 38, which comprises a processing unit communicating with one or more memories. Typically, the elements may be connected by cables to the processing circuitry 38, for example, radiators 26 may be connected by a cable 58 to the processing circuitry 38. Alternatively, or additionally, the elements may be coupled wirelessly to the processing circuitry 38. The processing circuitry 38 may be mounted in a console 50, which comprises operating controls 51 that typically include a keypad and/or a pointing device such as a mouse or trackball. The console 50 also connects to other elements of the medical procedure system 20, such as a proximal end 52 of the medical instrument 28. A physician 54 uses the operating controls 51 to interact with the processing circuitry 38 while performing the procedure, and the processing circuitry 38 may present results produced by system 20 on a display 56.

In some embodiments, prior to performing the medical procedure, CT images of the patient 22 are acquired. The CT images are stored in a memory (not shown) for subsequent retrieval by the processing circuitry 38. In FIG. 1, the display 56 is shown displaying various views 59 of a previous CT scan (or other suitable scan) which may be used as an aid for the physician 54 to guide the medical instrument 28 in the body-part. The display screen 56 also shows an image 61 captured by a camera (not shown) of the medical instrument 28. The CT images may be registered with the magnetic coordinate system so that a representation of the medical instrument 28 may be displayed with the CT images on the display 56 as will be described in more detail with reference to FIGS. 7 and 8.

In practice, some or all of these functions of the processing circuitry 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figure 3:
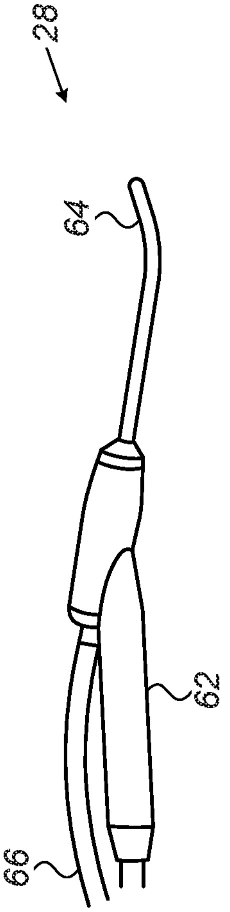
FIG. 3 is a schematic view of a medical instrument for use in the system of FIG. 1.
Figure 4:
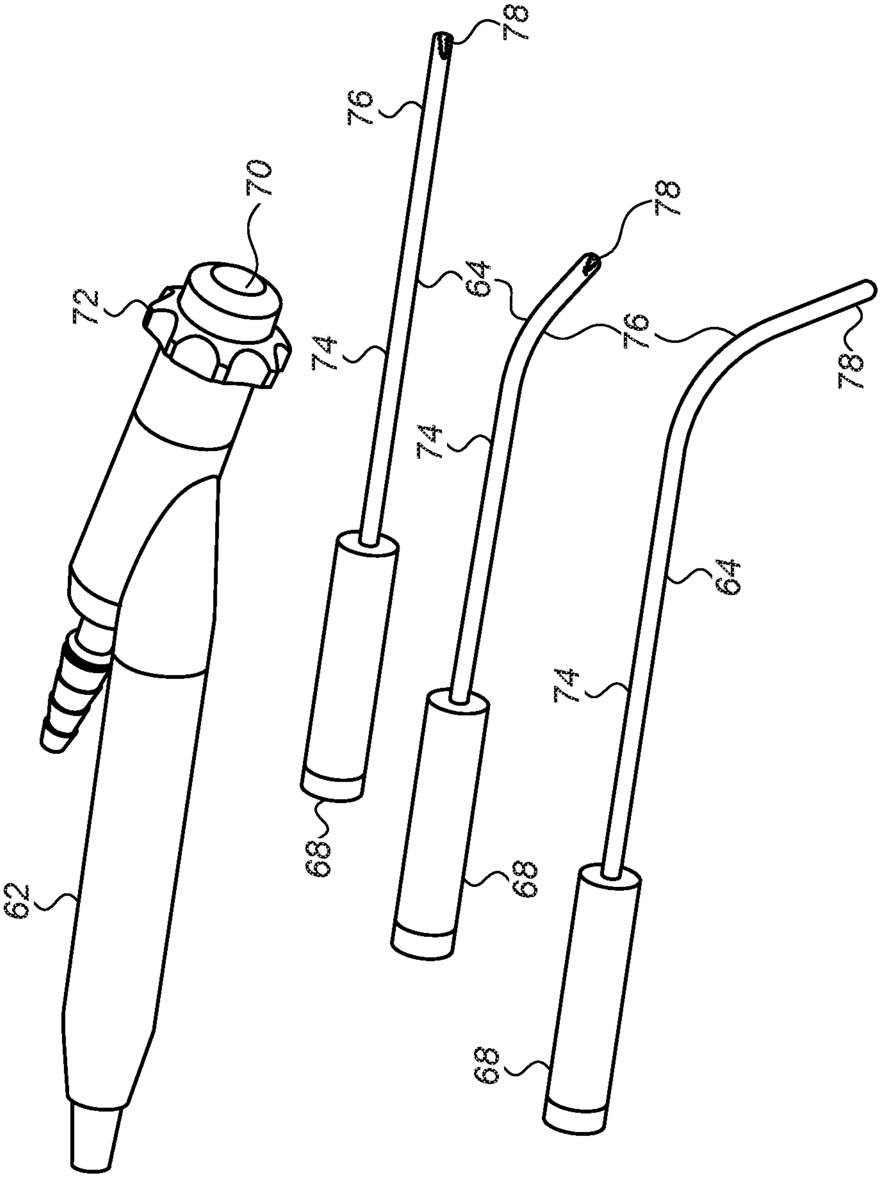
FIG. 4 shows a handle and interchangeable heads of the medical instrument of FIG. 3.

Reference is now made to FIG. 3, which is a schematic view of the medical instrument 28 for use in the system 20 of FIG. 1. The medical instrument 28 includes a handle 62 in which a plurality of different rigid interchangeable heads 64 are individually reversibly insertable. FIG. 3 shows one of the interchangeable heads 64 inserted into the handle 62. Other ones of the interchangeable heads 64 are shown in FIG. 4, which is described hereinbelow. The medical instrument 28 shown in FIG. 3 also includes an irrigation or drainage tube 66.

The medical instrument 28 shown in FIG. 3 is shown prior to any position-tracking transducers being added to the medical instrument 28. In fact, in some embodiments, the medical instrument 28 may be implemented with an off-the-shelf medical instrument which is sold without position transducers or sensors and to which position-tracking transducers are added at appropriate positions, as will be described below with reference to FIG. 5. For example, the S120 hand-piece and interchangeable reusable blades of Bien Air®, which is available without position transducers, may be adapted to provide the medical instrument 28 described hereinbelow. In other embodiments, the medical instrument 28 may be implemented as a purpose-built medical instrument with integral position-tracking transducers.

Reference is now made to FIG. 4, which shows the handle 62 and multiple different interchangeable heads 64 of the medical instrument 28 of FIG. 3. The handle 62 and the interchangeable heads 64 shown in FIG. 4 are also shown without the position-tracking transducers. The interchangeable heads 64 are different from each other with respect to a head shape and/or a head size.

Each interchangeable head 64 includes a plastic proximal end 68 which is inserted into a socket 70 of the handle 62. The socket 70 of the handle 62 includes multiple rotational positions in which to insert the different rigid interchangeable heads 64. For example, with the S120 hand-piece, the reusable blades may be inserted in eight different rotational positions. In some embodiments, the interchangeable heads 64 may be inserted into the socket 70 in a single rotational position.

The handle 62 includes multiple rotational positions to which to rotate the different rigid interchangeable heads 64. Therefore, once one of the interchangeable heads 64 has been inserted into the socket 70, the inserted interchangeable head 64 may be rotated to multiple rotational positions using a rotational adjustment cog wheel 72. In other embodiments, the inserted interchangeable head 64 cannot be rotated to another position.

In the example of FIG. 4, each of the interchangeable heads 64 is implemented with an elongated shaft 74 having a distal end 76, which includes at least one cutting element 78 disposed at the distal end 76 of the elongated shaft 74. The cutting element(s) 78 may include a shaving bur (e.g., a rough surface cylindrical shape or ball shape element) or a shaving blade rotating inside the elongated shaft 74 or any other suitable cutting element.

Figure 5:
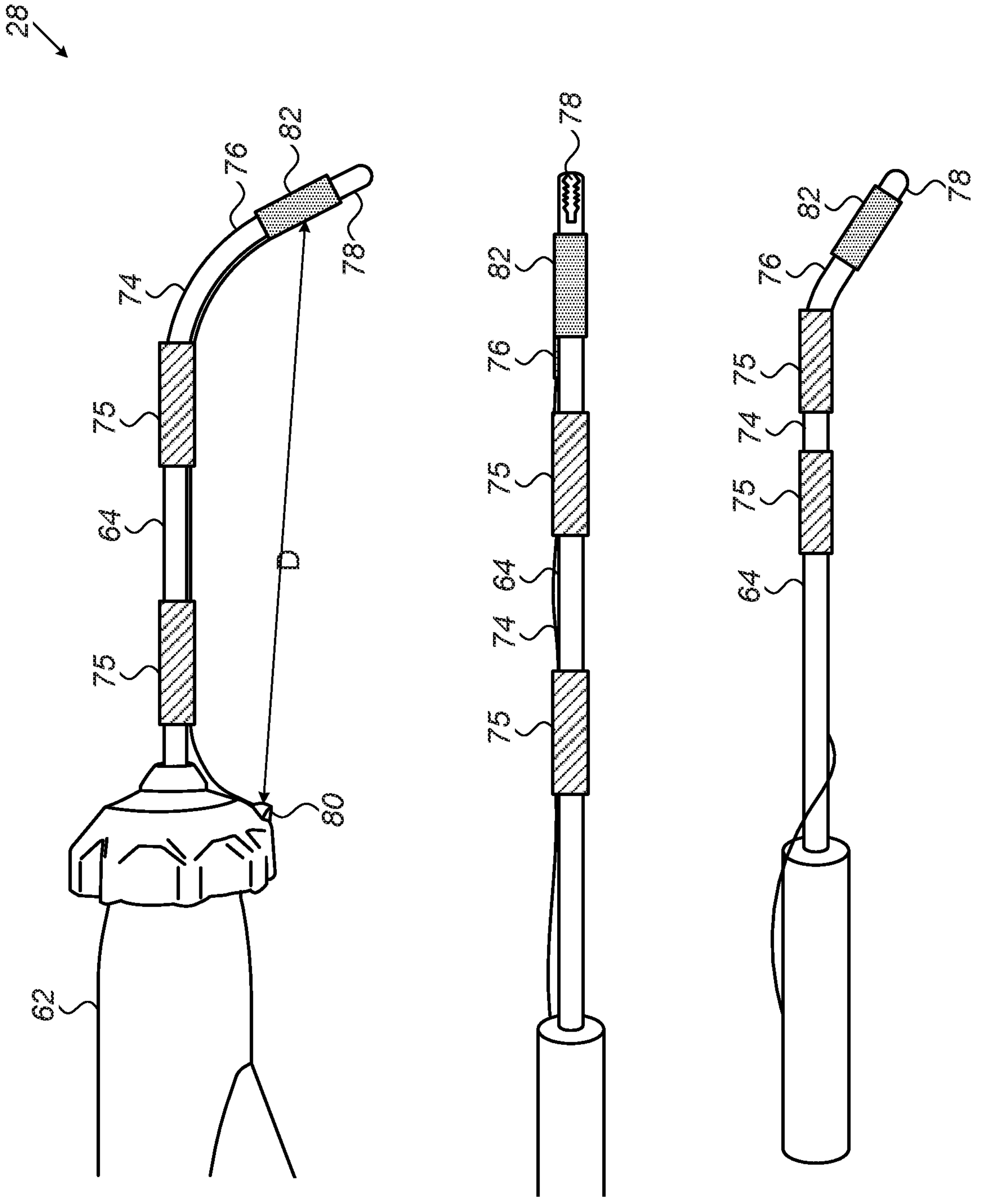
FIG. 5 shows transducers disposed on the handle and interchangeable heads of the medical instrument of FIG. 3.

Reference is now made to FIG. 5, which shows transducers 80, 82 disposed on the handle 62 and interchangeable heads 64 of the medical instrument 28 of FIG. 3. The handle 62 has a handle position-tracking transducer 80 disposed thereon. The handle position-tracking transducer 80 may include a dual or triple axis transducer, which can be used to detect a location, and orientation (including roll) of the handle 62. In some embodiments, the handle position-tracking transducer 80 may include at least one coil, for example two or three orthogonally placed coils.

Each interchangeable head 64 includes a head position-tracking transducer 82 disposed thereon at the distal end 76 of the elongated shaft 74 of the interchangeable head 64. The head position-tracking transducer 82 is electrically insulated from the elongated shaft 74 and the cutting element(s) 78. Wires extending from the head position tracking transducer 82 are secured, for example using self-adhesive tape 75, to the elongated shaft 74.

In some embodiments, the head position-tracking transducer 82 of each interchangeable head 64 may include at least one coil. The head position-tracking transducer 82 of each interchangeable head 64 may include a dual-axis transducer (for example, comprising two orthogonally placed coils) which can be used to detect a location, and orientation (including roll) of that interchangeable head 64. The head position-tracking transducer 82 may be printed on one or two printed circuit boards. For example, two coils may be printed on one or two printed circuit boards which are connected to the distal end 76 of the elongated shaft 74 so that each of the coils is orthogonal to the other. Printing the coils onto printed circuit board provides a more compact and more standard transducer than using wound coils. The coils may be coated with an electrically insulating material.

The handle position-tracking transducer 80, and the head position-tracking transducer 82 of each interchangeable head 64, are configured to detect at least part of the transmitted alternating magnetic fields of the magnetic field radiators 26 (FIG. 2).

At least some of the elongated shaft 74 may disposed in a plastic biocompatible sleeve prior to inserting the elongated shaft 74 in a body part. In some embodiments, the sleeve may cover the elongated shaft 74 from the plastic proximal end 68 up to and including the head position-tracking transducer 82.

The head position-tracking transducers 82 are strategically placed on the interchangeable heads 64 so that when each interchangeable head 64 is individually inserted into the handle 62, the relative position between the handle position-tracking transducer 80 and the head position-tracking transducer 82 of the inserted interchangeable head 64 uniquely identifies the inserted interchangeable head 64 irrespective of the rotational position in which the interchangeable head 64 has been inserted into the handle 62 and irrespective of the rotational position to which the interchangeable head 64 has been rotated. The relative position may include: (i) a distance D between the handle position-tracking transducer 80 and one of the head position-tracking transducers 82; and/or (ii) a relative orientation (which may or may not include roll) between the handle position-tracking transducer 80 and one of the head position-tracking transducers 82.

Therefore, different respective ones of the interchangeable heads 64 having differently positioned respective head position-tracking transducers 82 disposed thereon (on the distal end 76 of the respective head 64) so as when the different respective ones of the interchangeable heads 64 are inserted into the handle 62, the different respective head position-tracking transducers 82 define different respective positions relative to the handle position-tracking transducer 80.

Figure 6:
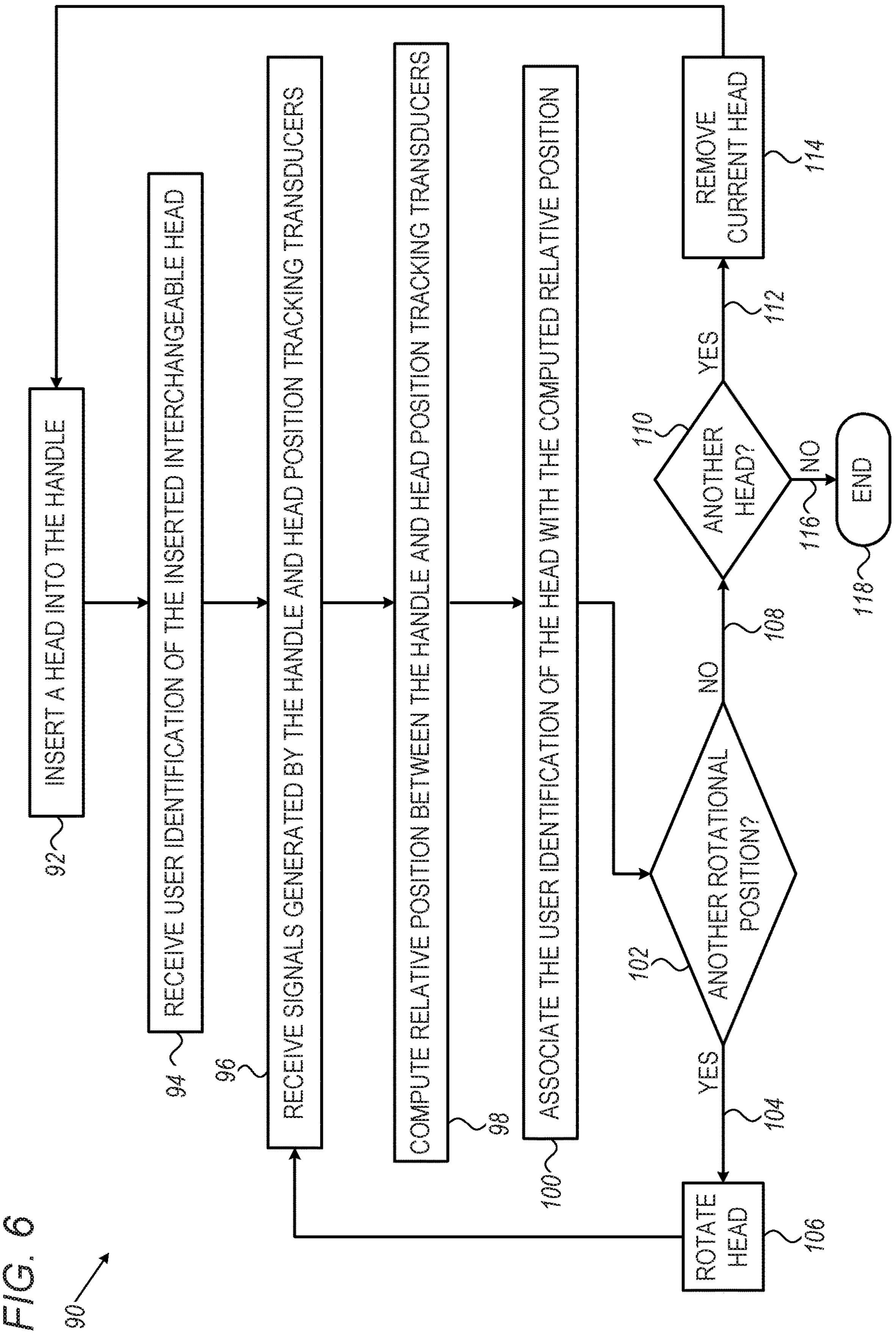
FIG. 6 is a flowchart including exemplary steps in a calibration method of the medical instrument of FIG. 5.

Reference is now made to FIG. 6, which is a flowchart 90 including exemplary steps in a calibration method of the medical instrument 28 of FIG. 5. Reference is also made to FIG. 5. One of the interchangeable heads 64 is inserted (block 92) into the handle 62. The processing circuitry 38 is configured to receive (block 94) a user identification of the inserted interchangeable 64 head via a user input device (e.g., the operating controls 51 (FIG. 1).

The processing circuitry 38 (FIG. 1) is configured to receive (block 96) signals generated by the handle position-tracking transducer 80 and the respective head position-tracking transducer 82 of the respective one of the interchangeable heads 64 inserted into the handle 62. The processing circuitry 38 is configured to compute (block 98) a relative position between the handle position-tracking transducer 80 and the head position-tracking transducer 82 of the inserted interchangeable head 64 responsively to the received signals. The computed relative position may include: (i) a computed distance D between the handle position-tracking transducer 80 and the head position-tracking transducer 82 of the inserted interchangeable head 64; and/or (ii) a computed relative orientation (which may or may not include roll) between the handle position-tracking transducer 80 and the head position-tracking transducer 82 of the inserted interchangeable head 64.

The processing circuitry 38 is configured to associate (block 100) the user identification of the inserted interchangeable head 64 with the computed relative position (e.g., the computed distance and/or the computed relative orientation) so as to allow future identification of the inserted interchangeable head 64 being reinserted into the handle responsively to a new computed relative position (e.g., a new computed distance and/or a new computed relative orientation) being within a given tolerance of the computed relative position (e.g., the computed distance and/or the computed relative orientation). The given tolerance may be any suitable value, for example, the given tolerance may be in the range of 0.1 mm to 5 mm and/or an angular orientation tolerance of up to 5 or 10%.

At a decision block 102, the processing circuitry 38 renders a question to the display 56 asking the user whether there is another rotational position in which to insert the interchangeable head 64 or to which to rotate the inserted interchangeable head 64. The user provides a response via the operating controls 51 for receipt by the processing circuitry 38. If the user responds that there is another rotational position (branch 104), the user rotates (block 106) the inserted interchangeable head 64 to a new rotational position and the method continues with the step of block 96. When the inserted interchangeable head 64 may be rotated freely with respect to the handle 62, the user may indicate this to the response of the rendered question at the step of block 102 and then continuously rotate the inserted interchangeable head 64 while the steps of blocks 96 to 100 are repeated for the different rotational positions of the inserted interchangeable head 64. If the user responds that there are no more rotational positions (branch 108), the processing circuitry 38 renders (block 110) a question to the display 56 asking the user whether there are more interchangeable heads 64 to calibrate. The user responds to the question. If there are more interchangeable heads 64 to calibrate (branch 112), the current head is removed (block 114) and a new interchangeable head 64 is inserted in the step of block 92 and the steps in the flowchart 90 are followed as described above. If there are no more interchangeable heads 64 to calibrate (branch 116) the method ends (block 118).

The above calibration method may include an additional step to check whether the computed relative position between the handle position-tracking transducer 80 and the head position-tracking transducer 82 for an inserted interchangeable head 64 is the same as, or within a given tolerance of, a previously computed relative position between the handle position-tracking transducer 80 and the head position-tracking transducer 82 of another one of the interchangeable heads 64. If the computed relative position, is the same as, or within a given tolerance of, the previously computed relative position between the handle position-tracking transducer 80 and the head position-tracking transducer 82 of another one of the interchangeable heads 64, the processing circuitry 38 may render a message to the display 56 informing the user that the current placement of the head position-tracking transducer 82 should be changed.

The calibration data is saved in a table for later use during operation of the system 20 described below with reference to FIG. 7.

Figure 7:
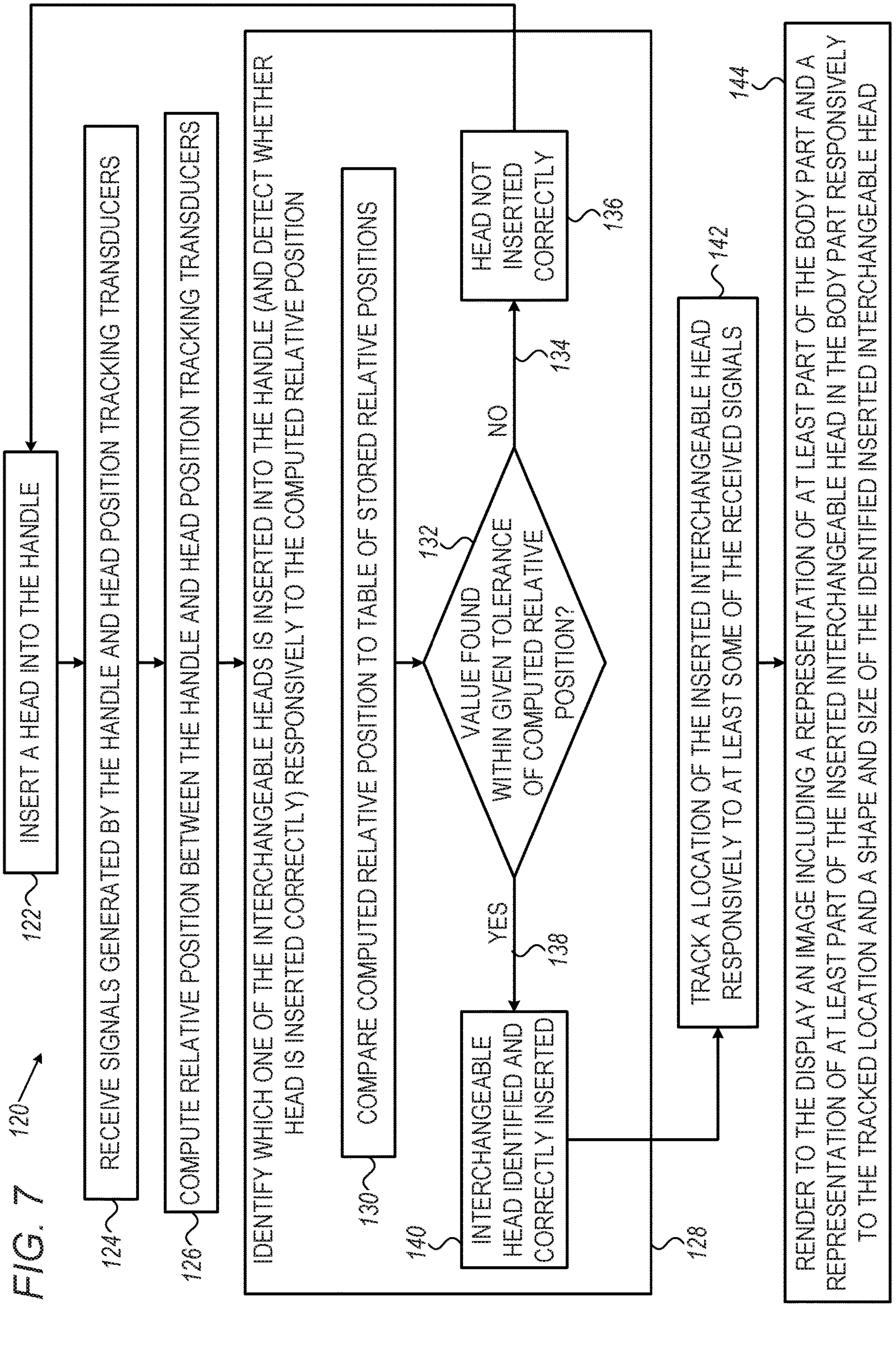
FIG. 7 is a flowchart including exemplary steps in a method of operation of the medical procedure system of FIG. 1.

Reference is now made to FIG. 7, which is a flowchart 120 including exemplary steps in a method of operation of the medical procedure system 20 of FIG. 1. Reference is also made to FIG. 5. The physician 54 inserts (block 122) one of the interchangeable heads 64 into the handle 62. The processing circuitry 38 (FIG. 1) is configured to receive (block 124) signals generated by the handle position-tracking transducer 80 and the respective head position-tracking transducer 82 of a respective one of the interchangeable heads 64 inserted into the handle. The processing circuitry 38 is configured to compute (block 126) a relative position (e.g., distance and/or orientation) between the handle position-tracking transducer 80 and the head position-tracking transducer 82 of the inserted interchangeable head 64 responsively to the received signals. The processing circuitry 38 is configured to identify (block 128) which one of the interchangeable heads 64 is inserted into the handle responsively to the computed relative position (e.g., distance and/or orientation) and optionally whether the interchangeable head 64 is inserted correctly into the handle 62 responsively to the computed relative position. The step of block 128 includes sub-steps now described below.

The processing circuitry 38 is configured to compare (block 130) the computed relative position to values in the table of stored relative positions and associated interchangeable heads 64. At a decision block 132, the processing circuitry 38 determines whether the table includes a value that is within a given tolerance of the computed relative position. If there is not a value (branch 134) in the table within a given tolerance of the computed relative position, the processing circuitry 38 may render (block 136) a message to the display 56 indicating that the interchangeable head 64 is not recognized or is not inserted into the handle 62 correctly. Processing then continues with the step of block 122.

If there is a value (branch 138) in the table within a given tolerance of the computed relative position, the interchangeable head 64 is identified (block 140) as the interchangeable head 64 associated with the value in the table and the inserted interchangeable head 64 is identified as being correctly inserted into the handle 62.

The processing circuitry 38 is configured to track (block 142) a location of the inserted interchangeable head 64 responsively to at least some of the received signals. The signals used to track the location of the inserted interchangeable head 64 may be based on the signals received from the handle position-tracking transducer 80 and/or the signals received from the head position-tracking transducer 82 of the inserted interchangeable head 64. When the interchangeable heads 64 may be rotated freely, for example, using the cog wheel 72 (FIG. 4), the location of the inserted interchangeable head 64 is generally tracked based at least on the signals received from the head position-tracking transducer 82 of the inserted head 64.

Figure 8:
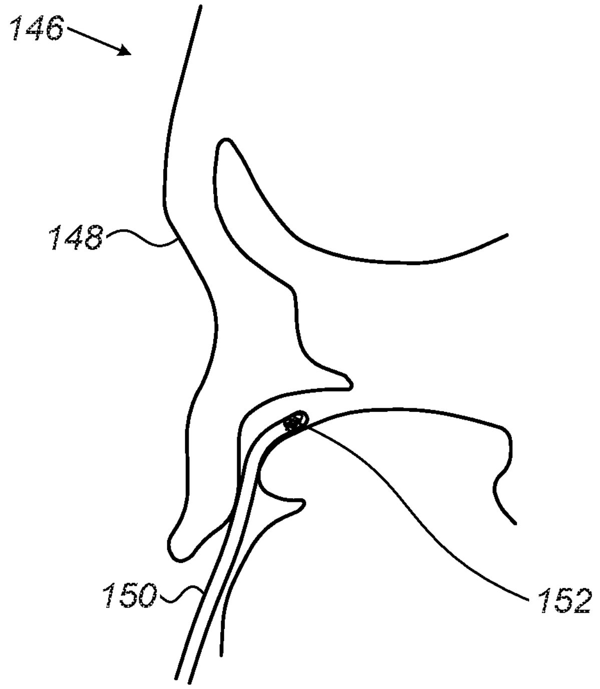
FIG. 8 is a schematic view of an image of a representation of a body part and an inserted interchangeable head rendered by the medical procedure system of FIG. 1.

Reference is now made to FIG. 8, which is a schematic view of an image 146 of a representation 148 of a body part and a representation 150 of an inserted interchangeable head 64 rendered by the medical procedure system 20 of FIG. 1. Reference is also made to FIGS. 5 and 7. The processing circuitry 38 is configured to render (block 144) to the display 56 (FIG. 1) the image 146 including the representation 148 of at least part of the body part and the representation 150 of at least part of the inserted interchangeable head 64 of the medical instrument 28 in the body part responsively to the tracked location and a shape and size of the identified inserted interchangeable head 64. As the interchangeable heads 64 are rigid, the representation 150 of the inserted interchangeable head 64 may be rendered based on a position of a single point of the inserted interchangeable head 64 and a known shape and size of the identified inserted interchangeable head 64. The cutting element(s) 78 may also be indicated using an indicator 152 on the representation 150.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical instrument tracking system, comprising:

a medical instrument including a handle and different rigid interchangeable heads, each rigid interchangeable head having a shaft with a proximal end and a distal end, each proximal end of each shaft being configured for individual insertion into a distal end of the handle, the handle having a handle position-tracking transducer disposed thereon, each distal end of each shaft having a head position-tracking sensor such that different respective ones of the interchangeable heads have differently positioned respective head position-tracking transducers disposed on the respective shafts so as when the proximal ends of the different respective ones of the interchangeable heads are inserted into the distal end of the handle, the different respective head position-tracking transducers define different respective positions relative to the handle position-tracking transducer; and processing circuitry configured to:

receive signals generated by the handle position-tracking transducer and the respective head position-tracking transducer of a respective one of the interchangeable heads inserted into the handle;

compute a relative position between the handle position-tracking transducer and the head position-tracking transducer of the inserted interchangeable head responsively to the received signals; and identify which one of the interchangeable heads is inserted into the handle responsively to the computed relative position.

2. The system according to claim 1, wherein the interchangeable heads are different from each other with respect to at least any one or more of the following: a head shape; or a head size.

3. The system according to claim 1, wherein the processing circuitry is configured to detect whether the inserted interchangeable head is inserted correctly into the handle responsively to the computed relative position.

4. The system according to claim 1, wherein the computed relative position includes a computed distance between the handle position-tracking transducer and the head position-tracking transducer of the inserted interchangeable head, the processing circuitry being configured to identify which one of the interchangeable heads is inserted into the handle responsively to at least the computed distance.

5. The system according to claim 4, wherein the handle includes multiple rotational positions in which to insert the different rigid interchangeable heads, the computed relative position includes a computed orientation of the head position-tracking transducer of the inserted interchangeable head relative to the handle position-tracking transducer, the processing circuitry being configured to identify which one of the interchangeable heads is inserted into the handle responsively to the computed distance and the computed orientation.

6. The system according to claim 4, wherein the handle includes multiple rotational positions to which to rotate the different rigid interchangeable heads, the computed relative position including a computed orientation of the head position-tracking transducer of the inserted interchangeable head relative to the handle position-tracking transducer, the processing circuitry being configured to identify which one of the interchangeable heads is inserted into the handle responsively to the computed distance and the computed orientation.

7. The system according to claim 1, wherein each of the interchangeable heads includes at least one cutting element.

8. The system according to claim 1, wherein the medical instrument is configured for inserting into a body part of a living subject, the system further comprising a location pad having at least one magnetic field radiator configured to transmit alternating magnetic fields into a region where the body-part is located, the head position-tracking transducer of each of the interchangeable heads including at least one coil configured to detect at least part of the transmitted alternating magnetic fields.

9. The system according to claim 8, wherein the head position-tracking transducer of each of the interchangeable heads is a dual axis transducer printed on a circuit board.

10. The system according to claim 1, wherein the medical instrument is configured for inserting into a body part of a living subject, the system further comprising a display, the processing circuitry being configured to:

track a location of the inserted interchangeable head responsively to at least some of the received signals; and render to the display an image including a representation of at least part of the body part and a representation of at least part of the inserted interchangeable head of the medical instrument in the body part responsively to the tracked location and a shape and size of the identified inserted interchangeable head.

11. A medical instrument tracking system, comprising:

a medical instrument including a handle and different rigid interchangeable heads for individual insertion into the handle, the handle having a handle position-tracking transducer disposed thereon, different respective ones of the interchangeable heads having differently positioned respective head position-tracking transducers disposed thereon so as when proximal ends of the different respective ones of the interchangeable heads are inserted into a distal end of the handle, the different respective head position-tracking transducers define different respective distal positions relative to the handle position-tracking transducer; and processing circuitry configured to:

receive signals generated by the handle position-tracking transducer and the respective head position-tracking transducer of a respective one of the interchangeable heads inserted into the handle;

compute a relative position between the handle position-tracking transducer and the head position-tracking transducer of the inserted interchangeable head responsively to the received signals;

receive a user identification of the inserted interchangeable head via a user input device; and associate the user identification of the inserted interchangeable head with the computed relative position so as to allow future identification of the inserted interchangeable head being reinserted into the handle responsively to a new computed relative position being within a given tolerance of the computed relative position.

12. The system according to claim 11, wherein the computed relative position includes a computed distance between the handle position-tracking transducer and the head position-tracking transducer of the inserted interchangeable head, the processing circuitry being configured to associate the user identification of the inserted interchangeable head with the computed distance so as to allow future identification of the inserted interchangeable head being reinserted into the handle responsively to at least a new computed distance being within a given tolerance of the computed distance.

13. The system according to claim 12, wherein the handle includes multiple rotational positions in which to insert the different rigid interchangeable heads, the computed relative position includes a computed orientation of the head position-tracking transducer of the inserted interchangeable head relative to the handle position-tracking transducer, the processing circuitry being configured to associate the user identification of the inserted interchangeable head with the computed distance and the computed orientation so as to allow future identification of the inserted interchangeable head being reinserted into the handle responsively to a new computed distance and a new computed orientation being within at least one given tolerance of the computed distance and the computed orientation, respectively.

14. The system according to claim 12, wherein the handle includes multiple rotational positions to which to rotate the different rigid interchangeable heads, the computed relative position including a computed orientation of the head position-tracking transducer of the inserted interchangeable head relative to the handle position-tracking transducer, the processing circuitry being configured to associate the user identification of the inserted interchangeable head with the computed distance and the computed orientation so as to allow future identification of the inserted interchangeable head being reinserted into the handle responsively to a new computed distance and a new computed orientation being within at least one given tolerance of the computed distance and the computed orientation, respectively.

15. A method for medical treatment using a medical instrument including a handle and different rigid interchangeable heads for individual insertion into the handle, the handle having a handle position-tracking transducer disposed thereon, different respective ones of the interchangeable heads having differently positioned respective head position-tracking transducers disposed thereon so as when the different respective ones of the interchangeable heads are inserted into the handle, the different respective head position-tracking transducers define different respective positions relative to the handle position-tracking transducer, wherein the medical instrument is configured for inserting into a body part of a living subject, the method comprising:

receiving signals generated by the handle position-tracking transducer and the respective head position-tracking transducer of a respective one of the interchangeable heads inserted into the handle;

computing a relative position between the handle position-tracking transducer and the head position-tracking transducer of the inserted interchangeable head responsively to the received signals;

identifying which one of the interchangeable heads is inserted into the handle responsively to the computed relative position;

transmitting alternating magnetic fields into a region where the body-part is located, the head position-tracking transducer of each of the interchangeable heads includes at least one coil; and detecting at least part of the transmitted alternating magnetic fields by the at least one coil.

16. The method according to claim 15, wherein the interchangeable heads are different from each other with respect to at least any one or more of the following: a head shape; or a head size.

17. The method according to claim 15, further comprising detecting whether the inserted interchangeable head is inserted correctly into the handle responsively to the computed relative position.

18. The method according to claim 15, wherein the computed relative position includes a computed distance between the handle position-tracking transducer and the head position-tracking transducer of the inserted interchangeable head, wherein the identifying includes identifying which one of the interchangeable heads is inserted into the handle responsively to at least the computed distance.

19. The method according to claim 18, wherein the handle includes multiple rotational positions in which to insert the different rigid interchangeable heads, the computed relative position includes a computed orientation of the head position-tracking transducer of the inserted interchangeable head relative to the handle position-tracking transducer, the identifying including identifying which one of the interchangeable heads is inserted into the handle responsively to the computed distance and the computed orientation.

20. The method according to claim 18, wherein the handle includes multiple rotational positions to which to rotate the different rigid interchangeable heads, the computed relative position including a computed orientation of the head position-tracking transducer of the inserted interchangeable head relative to the handle position-tracking transducer, the identifying including identifying which one of the interchangeable heads is inserted into the handle responsively to the computed distance and the computed orientation.

21. The method according to claim 15, wherein each of the interchangeable heads includes at least one cutting element.

22. The method according to claim 15, wherein the head position-tracking transducer of each of the interchangeable heads is a dual axis transducer printed on a circuit board.

23. The method according to claim 15, wherein the medical instrument is configured for inserting into a body part of a living subject, the method further comprising:

tracking a location of the inserted interchangeable head responsively to at least some of the received signals; and rendering to a display an image including a representation of at least part of the body part and a representation of at least part of the inserted interchangeable head of the medical instrument in the body part responsively to the tracked location and a shape and size of the identified inserted interchangeable head.

* * * * *